United States Patent [19]
Todd, Jr.

[11] Patent Number: 5,230,836
[45] Date of Patent: Jul. 27, 1993

[54] LOW MICRON-SIZED ASCORBIC ACID PARTICLES, ESPECIALLY A SUSPENSION THEREOF IN A MEDIUM IN WHICH THEY ARE INSOLUBLE, AND THE USE THEREOF AS AN ANTIOXIDANT FOR MEDIUMS IN WHICH THE PARTICLES REMAIN INSOLUBLE

[75] Inventor: Paul H. Todd, Jr., Kalamazoo, Mich.

[73] Assignee: Kalamazoo Holdings, Inc., Kalamazoo, Mich.

[21] Appl. No.: 717,926

[22] Filed: Jun. 20, 1991

[51] Int. Cl.$^5$ .................. A61K 35/78; A61K 31/355
[52] U.S. Cl. .................................. 252/407; 426/541; 426/544; 426/545; 426/546
[58] Field of Search ............... 252/389, 407; 426/541, 426/544, 545, 546

[56] References Cited

U.S. PATENT DOCUMENTS

| | | | |
|---|---|---|---|
| 3,316,101 | 4/1967 | Borenstein | 426/540 |
| 3,767,825 | 10/1973 | Hammes | 426/290 |
| 3,966,632 | 6/1976 | Colliopoulos | 426/309 |
| 4,352,746 | 10/1982 | Bracco et al. | 252/398 |
| 4,450,097 | 5/1984 | Nakatani et al. | 252/404 |
| 4,614,656 | 9/1986 | Tennikat | 426/61 |
| 4,883,679 | 11/1989 | Sewon | 426/532 |
| 4,913,915 | 4/1990 | Tanaka | 426/532 |
| 4,913,923 | 4/1990 | Van Den Ouweland | 426/533 |
| 4,915,961 | 4/1990 | Tanaka | 426/72 |
| 4,915,965 | 4/1990 | Tanaka | 426/282 |
| 4,925,681 | 5/1990 | Mai | 426/52 |
| 4,931,293 | 6/1990 | Cherukuri | 426/96 |
| 4,935,243 | 6/1990 | Borkan | 424/441 |
| 4,983,382 | 1/1991 | Wilmott | 426/62 |
| 5,077,869 | 12/1991 | Chang et al. | 426/541 X |
| 5,084,293 | 1/1992 | Todd, Jr. | 426/541 |
| 5,102,659 | 4/1992 | Hudson | 424/195.1 |

FOREIGN PATENT DOCUMENTS 326829 8/1989 European Pat. Off. .

OTHER PUBLICATIONS

Grindsted Brochure "Grindsted Functional Ingredients" (6 pages) GB A2-4US.
Grindsted Dimodan S Technical Data Sheet (2 pages) May 20, 1985.

*Primary Examiner*—Robert L. Stoll
*Assistant Examiner*—Valerie Fee
*Attorney, Agent, or Firm*—Gordon W. Hueschen

[57] ABSTRACT

Solid ascorbic acid particles of less than 38 microns in size are shown to be effective antioxidants for substrates in which ascorbic acid is insoluble, such as animal and vegetable oils, essential oils, carotenoids, and the like, at weight concentrations of 0.02% and even at 0.005% or below. These particles are preferably prepared by wet milling ascorbic acid in a medium in which it is insoluble, until the size is less than 38 microns, and preferably less. Employment of such particles in a medium in which they are insoluble, as well as employment in the stabilization of fats, oils, and foods, is demonstrated.

36 Claims, 2 Drawing Sheets

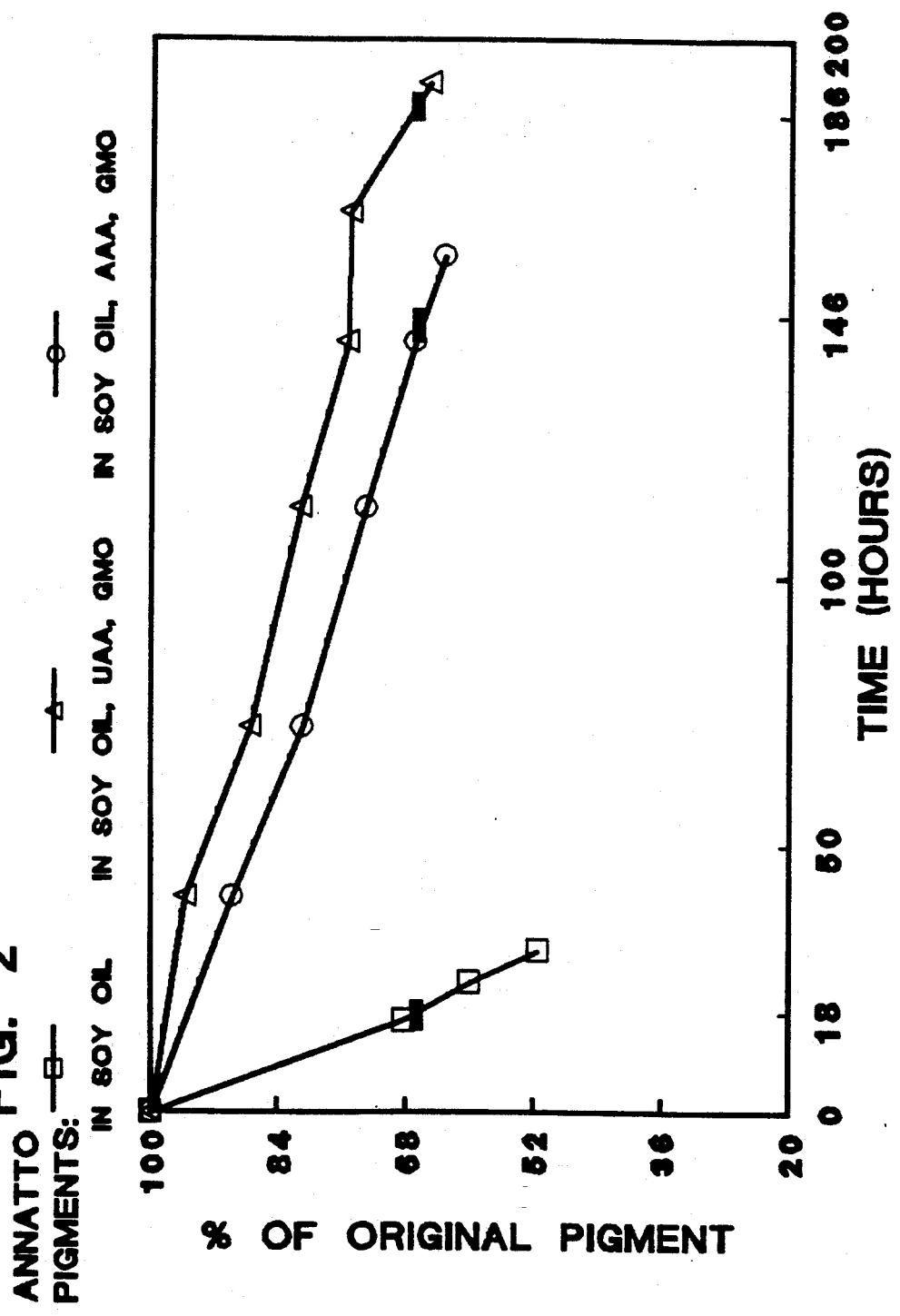

LOW MICRON-SIZED ASCORBIC ACID PARTICLES, ESPECIALLY A SUSPENSION THEREOF IN A MEDIUM IN WHICH THEY ARE INSOLUBLE, AND THE USE THEREOF AS AN ANTIOXIDANT FOR MEDIUMS IN WHICH THE PARTICLES REMAIN INSOLUBLE

FIELD OF THE INVENTION

Ascorbic acid and its use as an antioxidant for the stabilization of lipids, carotenoids, and the like against oxidation and color fading.

According to the present invention, oxidation of lipids and degradation of carotenoids is inhibited by solid particles of ascorbic acid which are below 38 microns in size, especially when suspended in an oleogenous substrate in which they are insoluble, or in a mixture with carotenoids and the like. The preparation and use of such solid ascorbic acid particles and of suspensions of such solid ascorbic acid particles is disclosed.

BACKGROUND OF THE INVENTION AND PRIOR ART

Oxidation of fats, vegetable oils, carotenoids and their biologically active, derivatives, Vitamin A, and of essential oils and other flavorings results in degradation of their quality, and is deleterious to foodstuffs containing the oxidized products.

The art shows many methods of inhibiting lipid oxidation by adding fat-soluble antioxidants to the substrate. The art does not show the stabilization of fats by the use of undissolved ascorbic acid particles of any size. The lipid-soluble antioxidants include synthetics, such as BHA and BHT, or natural antioxidants, such as Labiatae extracts, and particularly rosemary and sage extracts. Fat-soluble esters of ascorbic acid are also used. The synthetic antioxidants are normally dissolved in the fat at levels not to exceed their permitted limits of 0.02%, whereas the natural antioxidants may be used at higher levels if their flavor level is not objectionable in the particular food or fat. Tocopherols, being naturally present in vegetable oils, may be added to animal fats to increase stability. In vegetable oils, they act as pro-oxidants at levels above about 2000 ppm.

Ascorbic acid, which is water soluble and fat insoluble, is a common additive to foods, where it serves to increase the Vitamin C content. In citrus beverages, it has been claimed to improve the flavor, and in pickle brines to improve the freshness. An important use is in curing brines in combination with nitrates and nitrites. In the curing of the meat, it reacts to form nitrous oxides, which in turn react with heme pigments to form the stable red colors of cured meats. It has been suggested that it reduces the formation of nitrosamines during the cooking of such meats.

Ascorbic acid has been used as an antioxidant from time immemorial. However, a search in U.S. Patent Office classes and subclasses, namely, Class 426, Subclasses 96, 98, 250, 534, 536, 540, 541, 547, 638, and 654; Class 260, Subclass 398.5; Class 252, Subclasses 314 and 363.5; Class 585, Subclass 351; and Class 514, Subclass 772, revealed no suggestion of the present invention. An update of the search in the U.S. Patent Office Class 426, Subclasses 72, 541, 544, 545, 546, 653, and 654; Class 424, Subclass 441; and Class 106, Subclass 263, and I.P.C. B 29C 49/00, extending over approximately the past year, and references cited in related applications, revealed only the following developments:

Ascorbic acid has been dissolved in an aqueous algae solution prior to spray drying, where it may reduce degradation due to the stresses of that operation.

It has been dissolved in aqueous solutions of tea extract, to extend the antioxidant power of the tea.

It is used as an acidulant, either in beverages per se, or incorporated into a gum matrix including polyvinyl acetate which releases it slowly upon chewing of the gum.

It is less preferred than glucose-glucose oxidase/catalase as an oxygen scavenger in aqueous phases of emulsions, and it is used in aqueous solutions of cosmetics.

Solid ascorbic acid is used in vitamin tablets. In some applications, it may be coated with a fatty acid, to permit adhesion of the particles to the surface of a dried food. It may be a component in a fat plug in baker's margarine, wherein the plug is designed to keep the components included in it from undesirably affecting the flavor of the margarine, but assisting the baker when incorporated in a dough.

Encapsulation of carotenoids in gelatin is an accepted method of reducing the rate at which they degrade. Similar retardation of oxidation is achieved by encapsulating fats or other substances in capsules, or coating the particles with an oxygen and light barrier such as an opaque sugar layer.

It has been dissolved in ethanol, which in turn is added to a mixture of lecithin and tocopherols, to form a transparent liquid upon removal of the ethanol. This ternary composition of ascorbic acid is suggested for use in highly unsaturated fats, in which it exhibits greater effectiveness than mixtures of tocopherol and lecithin alone.

In my copending U.S. application Ser. No. 07/544,248, now U.S. Pat. No. 5,084,293 ascorbic acid has been dissolved in a volatile so such as methanol and water, and thence transferred into solution in a nonionic emulsifier, with the solvent subsequently being removed. This forms an "activated ascorbic acid," which has powerful antioxidant properties in oleogenous media or with carotenoids and the like. Other of my copending applications show synergistic mixtures of natural antioxidants and certain emulsifiers as stabilizers for carotenoids.

Solid ascorbic acid has not been used or suggested for use as an antioxidant or stabilizer for fats or carotenoids, so far as can be ascertained, because it is insoluble in lipid media.

OBJECTS OF THE INVENTION

It is an object of the present invention to provide a new solid particulate form of ascorbic acid, having a particle size less than about 38 microns on its largest dimension, the crystals thereof having irregular shapes, which is characterized by improved antioxidant and antifading properties in lipids, oils, carotenoids, and like fatty foods, flavors, and colors. Another object is the provision of such particles in an oleogenous medium in which they are insoluble. A further object is the provision of such compositions which also comprises a natural oil-soluble antioxidant, especially of the Labiatae genus. A further object is the provision of such compositions comprising also a non-ionic surface-active agent, which still further increases the antioxidant activity of such compositions. A still further object is the employment of such compositions in the stabilization of fats, fatty foods, and the like against oxidation and color fading, and another object is the provision of a fat or fatty food or other material so stabilized by the employment of a suitable stabilizing or antioxidant amount of either the novel solid ascorbic acid particles per se or in an oleogenous medium in which they are insoluble, optionally together with a natural antioxidant and/or a non-ionic surface-active agent or emulsifier, the fat or fatty material in any event being thus protected against oxidative degradation and color fading. Yet other objects will become apparent hereinafter and yet additional objects will be apparent to one skilled in the art.

SUMMARY OF THE INVENTION

My invention then comprises, inter alia, the following, singly or in combination:

An antioxidant composition consisting essentially of solid particles of ascorbic acid which are less than about 38 microns in size on their largest dimension; such a composition wherein at least about 50% of the solid particles of ascorbic acid are less than about 10 microns in size on their largest dimension; such a composition wherein essentially all of the particles are about 20 microns or less on their largest dimension; and such a composition comprising also a natural oil-soluble antioxidant. Moreover, a fat or oil composition, optionally containing a carotenoid, which is protected from oxidative degradation by a suspension of 0.001% or more by weight of ascorbic acid particles which are less than about 38 microns in size on their largest dimension; such a composition wherein at least about 50% of the solid particles of ascorbic acid are less than about 10 microns in size on their largest dimension; such a composition wherein at least about 50% of the solid particles of ascorbic acid are less than about 5 microns in size on their largest dimension and essentially all of the particles are about 20 microns or less on their largest dimension; and such a composition, optionally containing a carotenoid, which is protected from oxidative degradation by a suspension of 0.002% or more by weight of such ascorbic acid particles, and which optionally contains a natural oil-soluble antioxidant. Further, an antioxidant composition consisting essentially of a suspension of solid ascorbic acid particles in a medium, preferably in an edible oleogenous medium, in which they are insoluble, the solid particles of ascorbic acid being less than about 38 microns in size on their largest dimension; such an antioxidant composition wherein at least about 50% of the solid particles of ascorbic acid are less than about 10 microns in size on their largest dimension; such an antioxidant composition wherein at least about 50% of the solid particles of ascorbic acid are less than about 5 microns in size on their largest dimension; such an antioxidant composition wherein essentially all of the particles are about 20 microns or less on their largest dimension; such an antioxidant composition comprising also a natural oil-soluble antioxidant; such an antioxidant composition wherein the concentration of ascorbic acid particles of less than about 38 micron size in the medium is between about 5% and 50% by weight; and such an antioxidant composition wherein the ascorbic acid particles of less than about 38 micron size have irregular shapes and their concentration in the medium is between about 20% and 35% by weight. In addition, a fat or oil composition, optionally containing a carotenoid, which is protected from oxidative degradation by a suspension of 0.001% or more by weight of an antioxidant composition consisting essentially of a suspension of solid ascorbic acid particles, having a size less than about 38 microns on their largest dimension, in a medium, preferably an edible oleogenous medium, in which they are insoluble; such a composition wherein at least about 50% of the solid particles of ascorbic acid are less than about 10 microns in size on their largest dimension; such a composition wherein at least about 50% of the solid particles of ascorbic acid are less than about 5 microns in size on their largest dimension; such a composition wherein the antioxidant composition consists essentially of solid particles of ascorbic acid of about 20 microns or less in size on their largest dimension; such a composition wherein the composition comprises also a natural oil-soluble antioxidant; such a composition wherein the concentration of ascorbic acid particles of less than about 38 micron size in the medium is between about 5% and 50% by weight; and such a composition wherein the concentration of ascorbic acid in the medium is between about 10% and 35% by weight. Also, a method of protecting an edible or other fat, oil, carotenoid, fatty food, or other substrate which is lipid in nature or which comprises a lipid phase, comprising the step of admixing the said substrate with an oxidation-protective amount of any of the foregoing antioxidant compositions; such a method of protecting an edible fat, oil, and/or carotenoid by the addition thereto of at least about 0.002% by weight of solid ascorbic acid particles which are less than about 38 microns in size on their largest dimension; such a method wherein the protected substrate comprises a member selected from the group consisting of: soy oil; canola oil; peanut oil; sunflower oil; chicken fat; pork fat; turkey fat; beef fat; a marine oil; a paprika carotenoid; an annatto carotenoid; canthaxanthin; astaxanthin; and beta-carotene; such a method wherein the amount of the composition employed is calculated to provide an amount of microcrystalline ascorbic acid in the substrate of at least about 0.002% by weight; and such a method wherein a natural antioxidant taken from the class consisting of Labiatae extracts, tea extracts, and tocopherol is also added to the substrate or is present in the antioxidant composition employed. Also, a food or feed which is lipid in nature or which comprises a lipid phase in which the lipid or lipid phase is stabilized with an oxidation-protective amount of any of the foregoing antioxidant compositions; such a food or feed wherein the amount of the composition employed is calculated to provide an amount of microcrystalline ascorbic acid in the food or feed of above about 0.001% by weight; such a food or feed wherein the food or feed is protected with at least about 0.002% by weight of such solid ascorbic acid particles; such a food or feed wherein the food or fat comprises a member selected from the group consisting of: soy oil; canola oil; peanut oil; sunflower oil; chicken fat; pork fat; turkey fat; beef fat; a marine oil; a paprika carotenoid; an annatto carotenoid; canthaxanthin; astaxanthin; and beta-carotene; such a food or feed wherein the protective composition also comprises a natural oil-soluble antioxidant taken from the class consisting of Labiatae extracts, tea extracts, and tocopherol; and such a food or feed wherein the amount of protective microcrystalline ascorbic acid in the substrate is at least about 0.005% by weight. Additionally, a method of stabilizing the fatty phase of a cosmetic or an essential oil by admixing the fat with an oxidation-protective amount of an antioxidant composition consisting essentially of ascorbic acid particles which are less than about 38 microns in size on their longest dimension, optionally when suspended in a medium in which they are insoluble. Further, a method of stabilizing Vitamin A by admixing the Vitamin A with an oxidation-protective amount of an antioxidant composition consisting essentially of ascorbic acid particles which are less than about 38 microns in size on their longest dimension, optionally when suspended in an edible oleogenous medium in which they are insoluble. Finally such antioxidant particles suspended in a nonionic surface-active agent; and such antioxidant compositions including a nonionic surface-active agent; and a stabilized fat or oil composition wherein the stabilizing composition comprises a nonionic surface-active agent; and a stabilized fatty product wherein the stabilizing composition comprises an orally-ingestible nonionic surface-active agent; and such a stabilization method wherein the stabilizing composition comprises a nonionic surface-active agent; and such an antioxidant composition, stabilized product, and method wherein the surface-active agent is selected from the group consisting of
a. mono and di glycerides of fatty acids,
b. polyglyceride esters of fatty acids,
c. mono and diglyceride esters further esterified with a dibasic organic acid taken from the class consisting of citric, lactic, and tartaric acids,
d. acetylated mono and diglyceride esters further esterified with a dibasic organic acid taken from the class consisting of citric, lactic, and tartaric acids,
e. sorbitan esters of fatty acids,
f. propylene glycol esters of fatty acids, and
g. lecithin; and, finally, such an antioxidant composition, stabilized product, and
method wherein the surface-active agent comprises glycerol mono-oleate, sorbitan mono-oleate, sorbitan trioleate, sorbitan monostearate, octaglycerol mono-oleate, or decaglycerol capric caprylate.

GENERAL DESCRIPTION OF THE INVENTION

This invention discloses for the first time that a solid, undissolved particle of ascorbic acid, less than 38 microns in size, is an exceptionally powerful antioxidant for media in which the particles are insoluble. Unlike all of the prior art, it does not depend upon dissolution in a solvent such as water or alcohol to achieve its effectiveness. Indeed, one of the advantages of this invention is the avoidance of any solvent in the preparation of the antioxidant composition. Of critical importance is that the micron size of the particles be below about 38 microns on their largest dimension, and preferably below about 10 microns, and optimally the greatest part being below about 5 microns. Advantageously, all particles are below about twenty (20) microns on their greatest dimension. Ascorbic acid is a solid, which is readily soluble in water. To make it effective as a lipid antioxidant it must be reduced in size to below about 38 microns on its greatest dimension, as shown in the Examples, and the surface of the particles preferably wetted with an oleogenous material so that they will most advantageously act as an antioxidant. The reduction and wetting are advantageously performed by wet milling, such as in a paint mill or pebble mill. Less preferred is dry milling of granular ascorbic acid, since the <38 micron-sized particles must then be completely deaerated when mixed with the oil to be stabilized, to make them effective. Air may be occluded on their surfaces unless this precaution is taken.

Although, in aqueous systems, ascorbic acid has been reported to have pro-oxidant effects at high concentrations, in the lipid systems investigated this has not been the case. Accordingly, overdosing is not a risk. Since Vitamin C is an essential nutrient for both man and animals, and since in the gut the solid ascorbic acid particles present in the fat will be dissolved and absorbed as the fat is digested, it provides a positive nutrient effect as well as serving as an antioxidant. Furthermore, it is natural in its origin.

The Examples evidence the stabilization of a representative group of fats, oils, and carotenoids, as well as foods in which the fats or carotenoids are used. While extension of shelf life of foods is one objective of the invention, the reduction in degradation during present limited shelf storage is an even greater benefit, as it significantly improves the nutritional value of the food by delaying the development of fatty peroxides.

When formulated into a premix with carotenoids, the micron-sized ascorbic acid of the present invention acts both to stabilize the carotenoids and the fats in which they are dissolved or suspended when used in an animal feed. This result is not achieved effectively today even with available synthetic antioxidants.

Glossary of Terms

This glossary describes abbreviations and other technical terms and apparatus which may sometimes be referred to in this specification.

| Abbreviation | Technical Term |
|---|---|
| BHA | butylated hydroxy anisole |
| BHT | butylated hydroxy toluene |
| GMO | glycerol mono-oleate |
| SO | soy oil |
| SMO | sorbitan mono-oleate |
| STO | sorbitan trioleate |
| SMS | sorbitan monostearate |
| 8-1-0 | octaglycerol mono-oleate |
| 10-1-CC | decaglycerol mono-capric-caprylate |
| RM | rosemary extract, especially Herbalox-O ™ product of Kalsec, Inc., Kalamazoo, Michigan |

Peroxide Value: This is also a standard test for evaluation of the degree to which an oil has been oxidized.

Labiatae Extract: The solvent extract of a Labiatae herb, and preferably rosemary, sage, or thyme, especially rosemary. The preferable form is that described in Todd U.S. Pat. No. 4,877,635, and standardized to an antioxidant strength of about twice that of BHT in soy oil, under the standard Rancimat ™ conditions. It is commercially available in the form of Herbalox ™.

Rancimat ™: An instrument which measures the induction time of an oleogenous substrate, usually at 120 degrees Celsius and at 18 liters of air per hour. This is an accepted methodology for determining relative strengths of preparations of antioxidants. The effectiveness is expressed as the induction time of the sample divided by the induction time of the control, as a percent.

½ life: This is the time it takes for ½ of the color of a sample of a food color, e.g., annatto, bixin, paprika, or other carotenoid or dispersed carotenoid oleoresin, to fade under the conditions of the experiment. It is a highly-reproducible measurement, which is sufficiently accurate to evaluate the relative effectiveness of antioxidants and emulsifiers and synergistic combinations thereof. This technique will assist practitioners of the art to optimize formulations for specific uses.

Synergism: As defined in McGraw-Hill *Dictionary of Scientific and Technical Term:* "An action where the total effect of two active components is greater than the sum of their individual effects." For example, if one additive increases the ½ life by 10 hours, and a second by 20 hours, and the combination of the two by 50 hours, the synergistic effect is an additional (or plus) 20 hours.

Surface-Active Agent: In the context of this specification, it represents a nonionic surface-active agent, especially one taken from the class consisting of:
a. mono and di glycerides of fatty acids,
b. polyglyceride esters of fatty acids,
c. mono and diglyceride esters further esterified with a dibasic organic acid taken from the class consisting of citric, lactic, and tartaric acids,
d. acetylated mono and diglyceride esters further esterified with a dibasic organic acid taken from the class consisting of citric, lactic, and tartaric acids,
e. sorbitan esters of fatty acids,
f. propylene glycol esters of fatty acids, and
g. lecithin, and equivalents thereof.

RM Rosemary Extract: The extract used is Herbalox ™, which is a commercial product available from Kalsec, Inc., standardized as to antioxidant activity, and comprising about 20% active antioxidant compounds. It should be recognized, in this connection, that the art does not yet enable one to determine the exact concentration of active antioxidants in the extract, and 20% is merely an approximation based on the degree of dilution of the deodorized rosemary extract with soy oil.

BRIEF DESCRIPTION OF THE DRAWINGS

FIGS. 1 and 2 portray the fading curves of paprika and annatto pigments under controlled conditions. The percentage of the original color of the sample is plotted against time. Further details of the experiments are to be found in Example 4.

DETAILED DESCRIPTION OF THE INVENTION

Figure 1:
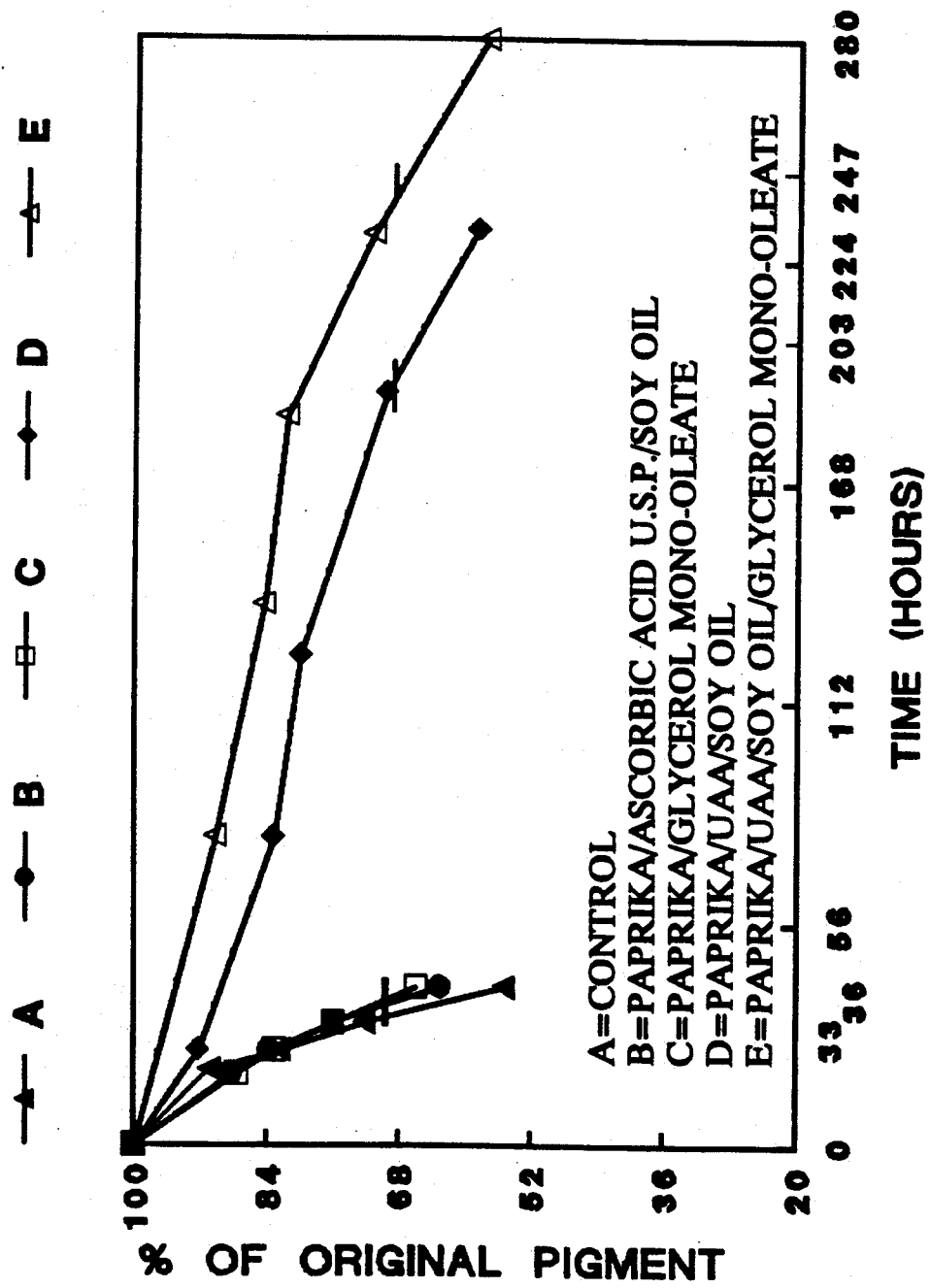

The following Examples are given by way of illustration only, and are not to be construed as limiting.

These Examples show the preparation of the novel solid ascorbic acid antioxidant, its effectiveness by itself and in synergistic combinations with other antioxidants and its use in preventing color loss with carotenoids. They portray its efficacy in a representative group of foods and feeds, as well as in essential oils and cosmetics, in such a manner that one skilled in the art may create forms of the invention best adapted to specific needs.

Where indicated, the Examples use a Rancimat ™ for the determination of the degree of stabilization of the substrate. This standard methodology involves blowing 18 liters of air per hour through a sample of an oil, measuring the conductivity in water of the gases generated, and determining when the oil has become rancid by the rate of change of conductivity. Higher temperatures are used for more stable oils, it being recognized that, for every ten degrees increase in temperature, the induction time decreases by about one-half. This standard methodology generates the same kind of induction curve as the standard TBA test. More sophisticated procedures, using chemiluminescence and electron spin resonance spectroscopy, show the same pattern of oxidation. Accordingly, the stabilization of lipids with solid ascorbic acid reduces the rate at which toxic hydroperoxides form, and can contribute to the nutritional safety of our food supply.

EXAMPLE 1

Preparation of Particles of Ascorbic Acid less than 38 Microns in Size (uAA), and Comparison of Antioxidant Activity with Prior Art The ascorbic acid of commerce is a white granular powder, similar in appearance to sugar but of smaller particle size. It is used as such, or impact milled to give a finer powder suitable for tableting. This powder has particles far greater than 38 microns in size on their largest dimension, usually about 180 microns on their largest dimension.

In the prior art applications, the mesh size of the ascorbic acid is not critical, since it is ultimately dissolved in water in the intended application as a nutrient and/or antioxidant. The only prior art advantage of finer powders is merely that of powdered sugar—the product is more compact, can be tableted more readily, and dissolves more quickly in the aqueous solution in which it is used as a nutrient or antioxidant.

In the new art described in this invention, the ascorbic acid is used as an antioxidant either per se or in a medium in which it is insoluble, and it is only effective in or out of such a medium if the particle size is less than about 38 microns. The mesh size is preferably below about 20 microns, and more preferably below 10 microns, with a substantial portion being below 5 microns. A solid ascorbic acid particle size wherein essentially all particles are 20 microns or less on their largest dimension is attainable and usually preferred.

<38 micron-sized ascorbic acid (uAA) may be prepared by grinding larger sized crystals (as in a mortar and pestle, or a hammer mill) and separating the <38 micron sized particles by sieving. Preferably, they are mixed with an oleogenous vehicle, in which the ascorbic acid is insoluble, and passed through a paint mill, or rolled as a suspension in oil in a pebble mill. Any of the other means of preparation of micron-sized particles known to the art are acceptable.

The micron-sized particles used in this and the following examples have except where otherwise indicated, been prepared by pulverizing in a pebble mill in an oil. The particle size is best determined by observation under a microscope, and these preparations consist of essentially all particles being less than about 15 microns, with more than half being less than 5 microns in size on their longest diameter. The particle size may also be determined by sieving. All were less than 20 microns on their greatest dimension, and the particles had irregular shapes.

The product used in this example was prepared by adding one part of granular ascorbic acid (AA) to three parts of soy oil, and pebble milling for 72 hours to make the <38 micron sized particles (uAA).

TABLE 1.1

Comparative Antioxidant Power of Micron-Sized Ascorbic Acid in Soy Oil, a Medium in which it is Insoluble

| Preparation | % Concentration of powder, uAA, BHA, or BHT in soy oil | Induction Time, Hours | Rancimat, 120° C., Ratio to Control |
|---|---|---|---|
| control | 0 | 3.45 | 1.00 |
| BHA | 0.02 | 3.51 | 1.02 |
| BHT | 0.02 | 3.62 | 1.05 |
| regular powder-AA | 0.05 | 4.12 | 1.19 |
| micron particles-uAA | 0.05 | 10.22 | 2.88 |
| ascorbyl palmitate | 0.05 | 5.96 | 1.73 |

Discussion

If glycerol mono-oleate is substituted for soy oil as the vehicle for milling the particles similar improvement in stability is observed.

In a similar test, at 113° C., the ratio of induction time of soy oil dosed with 0.005% uAA to the control was 1.38. This shows that the solid particles are effective at unconventionally low dose levels, far below the standard 0.02% permissible dose of oil-soluble synthetic antioxidants.

It is apparent that the <38 micron-sized ascorbic acid particles outperform even ascorbyl palmitate, an ascorbic fat-soluble ester of commerce, and that neither the commercial ascorbic acid nor the common synthetic antioxidants have significant effects. The uniqueness of this preparation is thus demonstrated.

EXAMPLE 2

Dose Response of Canola Oil to <38 Micron-Size Ascorbic Acid Particles, and Comparison with Other Antioxidants Canola oil, a highly-unsaturated and widely-used vegetable oil, was dosed with varying amounts of the pebble-milled ascorbic acid of Example 1. Substantially all of the particles were below 20 microns in size, and most were below 10 microns in size. Additionally, the canola oil was dosed with several standard antioxidants at the commonly used level of 0.02%.

The stability of the oil was determined by the standard procedure on the Rancimat, at 110° C.

The dose level and stability in hours are reported in Table 2-1, as well as the ratio of the hours of the sample to the hours of the control.

TABLE 2-1

Stability of Canola Oil Dosed with Different Levels of <38 Micron-Size Ascorbic Acid Particles, and with Other Antioxidants.

| Antioxidant | Dose, % | Stability hours | Ratio to control | |
|---|---|---|---|---|
| control | | 9.24 | 1.00 | |
| uAA | 0.001 | 9.80 | 1.06 | |
| uAA | 0.002 | 11.64 | 1.26 | |
| uAA | 0.005 | 12.25 | 1.32 | |
| uAA | 0.01 | 14.55 | 1.57 | |
| uAA | 0.01 | 14.75 | 1.59 | with 0.01% rosemary |

TABLE 2-1-continued

Stability of Canola Oil Dosed with Different Levels of <38 Micron-Size Ascorbic Acid Particles, and with Other Antioxidants.

| Antioxidant | Dose, % | Stability hours | Ratio to control |
|---|---|---|---|
| uAA | 0.02 | 15.90 | 1.66 |
| uAA | 0.05 | 23.64 | 2.55 |
| BHA | 0.02 | 9.79 | 1.06 |
| | 0.20 | 10.07 | 1.09 |
| BHT | 0.02 | 9.79 | 1.06 |
| AA palm. | 0.02 | 12.50 | 1.35 |

Similar dose response curves are obtained with fats. The addition of rosemary at 0.01% shows a slight improvement. In a marine oil or animal fat, the improvement is greater.

Discussion

The Table shows that there is a continuous increase in stability with increasing amounts of the micron-sized ascorbic acid particles, and that they do not become a pro-oxidant at higher concentrations, as do certain other natural antioxidants. It also shows that the insoluble ascorbic acid particles are orders of magnitude more effective than several times the same amount of the most commonly-used synthetic antioxidants, BHA and BHT. It is surprising that the uAA is about four times as effective as its fatty acid ester.

It further points out that, to achieve a stability equivalent to that obtained by these synthetics at their dose limits of 0.02% in foods, less than 0.005% uAA and even as low as 0.001% or 0.002% uAA, may be used, although 0.02%, 0.05%, 1.0% uAA or above may be employed where desired or indicated. Exceptionally low doses are also shown to be effective in soy oil, cf. Example 1.

While oleogenous or lipid media such as soy oil are preferred suspending media for the uAA particles in the antioxidant composition of the invention, other suspending media in which the uAA particles are insoluble, such as hexane, may also be employed, especially where non-food use of the antioxidant composition is contemplated.

EXAMPLE 3

Preparation and Use Acid Particles in the Stabilization of Soy Oil

Although the preferred procedure is to mill the ascorbic acid in a lipid medium, it can also be ground and directly added to the oil to be stabilized.

A commercial powdered ascorbic acid was ground in a mortar and pestle, and then selectively sieved through standard sieves to sort the particles according to their largest diameter. Because of a tendency of the smallest particles to stick together, the larger mesh sizes contain some smaller mesh particles and, therefore, in the table below, the 30 to 38 micron fraction contains some 20 to 30 and some less than 20 micron particles. However, this does not affect the conclusion that smaller particles are preferred.

<20, 20–30, and 30–38 micron particles were dosed into soy oil at 0.05% w/w, and the induction times of the dosed oils compared to that of the control oil at 120° C., using the Rancimat. The ratios as compared to the control were 2.8, 2.2, and 2.0 respectively, showing that even the 30–38 micron is effective, but that the <20 micron is much superior.

A second experiment was performed in which soy oil was dosed at 0.05% with a commercial fine ascorbic acid powder, and with the sieved <20 micron particles. The particles suspended in the oil were then centrifuged in a standard lab centrifuge for thirty minutes, and the stability of the supernatant oils compared. The oil dosed with the commercial powder had the same stability as the control, showing no improvement due to the ascorbic acid. That containing the <20 micron particles had an induction time of 4.3 hours as compared to the 3.5 hours of the control, showing substantial improvement due to solid ascorbic acid particles remaining in suspension as a very slight haze.

In a third experiment, ascorbic acid particles less than 30 microns in size were obtained by sieving a mortared powder. A portion of the particles were wet with soy oil by agitation and degassing. Both the wetted portion and the dry particles were added to soy oil at 0.02% w/w, and the induction times determined on the Rancimat at 120° C. The difference between the induction times of the two test samples and an undosed control was calculated, and it was found that the wetted particles were 128% as effective as the dry particles. This shows that the preferred form of the invention is wetted and degassed particles, which can be most easily obtained by wet milling.

EXAMPLE 4

Stabilization of Paprika Pigments with Particles of Ascorbic Acid less than 38 Microns in Size, and Synergistic Mixtures with Other Natural Antioxidants. Stabilization of other Carotenoids

Discussion

Paprika contains a mixture of carotenoid pigments, including hydrocarbons such as beta-carotene, and xanthophylls, such as capsanthin. Like any carotenoid, these substances are readily oxidized when exposed to air, and ethoxyquin is used by the art to stabilize them. Ethoxyquin is of questionable safety, and is not permitted as an antioxidant in any human food except paprika, where it may be used at levels of about 200 ppm. In animal feeds, it is permitted at 350 ppm.

Paprika pigments are fat soluble, and an extract, oleoresin paprika, is widely used in the food industry. Like ground paprika, this oleoresin fades rapidly when exposed to air and dispersed on a carrier, such as salt, dextrose, flour, and the like. A measure of effectiveness of an antioxidant is called the ½ life of the oleoresin when dispersed on flour salt, at a concentration of 2.7% of an oleoresin of 50,000 standard American Spice Trade Association color units. The ½ life is defined as the length of time required for ½ of the color to fade on a 2 gm. sample, held in a test tube at 65° C.

EXAMPLE 4-1

In this example, the oleoresin paprika is stabilized by adding an amount of a 25% suspension of <38 micron-sized ascorbic acid particles in soy oil, prepared by pebble milling the mixture of commercial powdered ascorbic acid and soy oil until the particles are less than 20 microns in size, and over half less than 10 microns in size.

This suspension is mixed thoroughly with the oleoresin paprika at a level of 5%, to give a concentration of 1.25% of the micron-sized ascorbic acid particles in the oleoresin.

To a portion of this mixture, a rosemary extract (RM), Herbalox (R), made by Kalsec, Inc., is added at a 2% level.

The ½ lives of the oleoresin dispersed on salt is measured by assaying the color on the salt in the test tubes, by the standard procedure of the American Spice Trade Association. (See Glossary.) They are reported in Table 4-1. Comparisons with standard synthetic oil-soluble antioxidants are shown. These include BHA, BHT, and ascorbyl palmitate (AP), a fat-soluble ester of ascorbic acid. Commercial ascorbic acid powder is also shown.

TABLE 4-1

½ lives of Oleoresin Paprika Containing Various Antioxidants

| Preparation | % antioxidant(s) | ½ Life hrs | increase hrs | syn hrs |
|---|---|---|---|---|
| Control | | 33 | | |
| BHT | 0.2 | 35 | 2 | |
| BHA | 0.2 | 36 | 3 | |
| AA commercial | 1.25 | 36 | 3 | |
| AP | 0.6 | 55 | 22 | |
| rosemary | 2.0 | 64 | 31 | |
| uAA | 0.5 | 93 | 60 | |
| uAA | 1.25 | 203 | 170 | |
| uAA + RM | 1.25 + 2.0 | 336 | 303 | 102 |
| uAA + GMO | 1.25 + 6.25 | 247 | 214 | |
| AA + GMO | 1.25 + 6.25 | 36 | 3 | |

Discussion

Like BHA and BHT, the ascorbic acid of commerce gives the paprika a ½ life and color stability which is only slightly higher than the control paprika. It is clear that only the micron-sized ascorbic acid particles have a dramatic effect, even though they are not soluble in the paprika. While the micron-sized ascorbic acid is exceptionally effective by itself, when combined with rosemary extract remarkable synergistic effects occur. The 102 hours color stability resulting from synergy is more than the hours gained by any of the other antioxidants, and is 330% of that added by the rosemary alone. This synergism is characteristic of other Labiatae extracts, such as those of sage and thyme. Such a Labiatae entirely natural system is many magnitudes better than any synthetic antioxidant, and it is particularly remarkable that the micron-sized ascorbic acid, which is insoluble in the oleoresin paprika and/or soy oil, is more effective than its fat-soluble ester, ascorbyl palmitate, and at a lower dose. The effectiveness and synergism are further enhanced by the addition of non-ionic emulsifiers, in which the ascorbic acid remains undissolved. In the above table, the effectiveness of glycerol monooleate (GMO) is shown. The commercial ascorbic acid was milled with GMO, and the micron-sized product added to the paprika oleoresin. The increase of 44 hours due to the GMO is significant. The range of utilizable emulsifiers is described in my copending application Ser. Nos. 07/525,340 now U.S. Pat. No. 5,059,435 and 07/525,342, now U.S. Pat. No. 5,079,016 and includes the nonionic surface-active agents mono- and di-glycerides of fatty acids, polyglyceride esters of fatty acids, mono- and di-glyceride esters further esterified with a dibasic organic acid taken from the class consisting of citric, tartaric, and lactic acids, sorbitan esters of fatty acids, and propylene glycol esters of fatty acids and especially mono- and di-glycerides, sorbitan fatty acid esters, glycerol mono-oleate, and mixed glycerol esters of fatty acids, citric acid, and/or tartaric acid, with specific preferred emulsifiers being a monoglyceride of a fatty acid or a polyglycerol ester of a fatty acid and more specifically, glycerol mono-oleate or decaglycerol capric-caprylate, some especially preferred nonionic surface-active agents being GMO, STO, SMO, SMS, 8-1-0, and 10-1-CC. Such surface-active agents can be advantageously included in any of the antioxidant compositions of the invention, and even to produce synergistic effects, as further disclosed and illustrated herein.

The same improvement over the prior art antioxidants is exhibited with other carotenoids, such as bixin, carrot extract, beta-carotene, and other synthetic carotenoids such as canthaxanthin, astaxanthin, and beta-apo-8-carotenal which are presently stabilized by encapsulation in gelatin.

EXAMPLE 4-2

For example, the ¾ life of a 1.35% w/w dispersion on flour salt of a 5% microcrystalline suspension of bixin was increased from 18 hours to 186 hours by the addition of 1.25% w/w of <38 micron-size ascorbic acid particles milled in glycerol mono-oleate (GMO) as prepared above. Activated ascorbic acid prepared according to my copending application, by dissolving the ascorbic acid in methanol, mixing with GMO, and desolventizing, gave a ¾ life of 146 hours. This is significantly below the stability achieved with the uAA. The addition of rosemary extract further extends the ¾ life. As in the case of paprika oleoresin, the commercial ascorbic acid powder is without effect, and the synthetic antioxidants are substantially less effective than the micron-sized ascorbic acid composition.

FURTHER REFERENCE TO THE DRAWINGS

FIGS. 1 and 2 show the fading curves of the above two carotenoids, and assist in visualization of the statements and data in the foregoing.

FIG. 1 shows that the control A, paprika (in soy oil), as well as B, paprika in soy oil with normal ascorbic acid particles, and C, paprika in glycerol mono-oleate, faded rapidly and had a ¾ life of less than 56 hours, whereas the paprika in soy oil in the presence of the micron-sized ascorbic acid of the present invention had a ¾ life in excess of 200 hours (203 hours) which could be further substantially extended (to 247 hours) by the inclusion of glycerol mono-oleate in the suspension with the micron-sized ascorbic acid particles.

FIG. 2 shows the rapid fading of annatto pigments such as bixin in soy oil, much less rapid fading of such pigments in glycerol mono-oleate containing the micron-sized ascorbic acid particles according to the invention and a substantially shorter ¾ life when the activated ascorbic acid dissolved in glycerol mono-oleate according to my prior invention is employed, the ¾ lives being 18 hours, 186 hours, and 146 hours, respectively.

From the above, it is clear that the <38 micron-size ascorbic acid particles are effective antioxidants for carotenoids, even though insoluble in the preparation. Furthermore, it is clear that synergistic effects are attained when the <38 micron-size ascorbic acid is combined with a natural antioxidant, such as rosemary, thyme, or sage, and that the effects are preserved or enhanced in the presence of non-ionic emulsifiers. Tea extract or tocopherol or other natural antioxidant may be used in place of rosemary with only slight disadvantage, e.g., lesser antioxidant power and/or discoloration as noted elsewhere herein. All of this is new to the art.

EXAMPLE 5

Stabilizing the Color of Seasoned Potato Chips

Potato chips were prepared commercially, and 25 gms were placed in paper bags. To these bags were added 5 gms of salt upon which 3.3% of a 40,000 color value oleoresin paprika had been predispersed. The oleoresin contained the levels of rosemary (RM) extract (Herbalox ™), tocopherols (T), <10 micron ascorbic acid particles (uAA), and soy lecithin noted in Table 4-1. In this case, the uAA was obtained by milling and was at a concentration of 26% by weight in soy oil. The samples which contained no lecithin did contain the equivalent amount of soy oil, which is commonly used as a standardization medium. Each sample was completely mixed. Preferably, the additives are also premixed and then added, but they can be added individually as well.

The colored potato chips were placed in clear plastic bags under fluorescent light of the quality used in food stores. They were exposed for two weeks at room temperature. Another portion of the chips was kept in the dark.

The chips stored in the light were then evaluated for color fading, aroma, and taste.

The results are as shown below.

TABLE 5-1

Composition and Stability of Colored Potato Chips.

| Composition of Oleoresin % | | | | | | | |
|---|---|---|---|---|---|---|---|
| RM | T | uAA | Lecithin | color | aroma | taste | acceptability |
| 0 | 0 | 0 | 0 | faded | rancid | rancid | reject |
| 3 | 0 | 3 | 0 | stable | fresh | oily | acceptable |
| 3 | 0 | 3 | 25 | stable | sl off | sl off | acceptable |
| 3 | 2.6 | 3 | 25 | stable | sl off | sl off | acceptable |

The color of the control did not fade as much in the dark, but the flavor ranking of the sample was similar to the 0000 sample exposed to the light.

It is clear that all of the combinations containing uAA held their color, while the control did not. The slightly off aromas of the samples containing lecithin were described as oily-nutty, and it should be noted that the addition of tocopherol did not effect the development of this defect. Although not shown, it is known that the rosemary extract by itself would improve the color and flavor stability. However, the combination thereof with micron-sized particles of ascorbic acid is synergistic in the improvement of stability.

Although the color of ground paprika is more stable than that placed on potato chips, it does fade when stored at room temperature. It may be stabilized in the same fashion as the oleoresin, by adding a premix consisting of the uAA in an oleogenous vehicle in which it is insoluble, such as partially hydrogenated fats, monodiglycerides, lecithin, and the like.

Such a premix preferably contains a rosemary, sage, or thyme extract, to achieve synergistic stabilizing effects.

EXAMPLE 6

Particle Size Distribution of Pebble-Milled Ascorbic Acid in Soy Oil

Commercial ascorbic acid powder was pebble milled for 96 hours, at a concentration of 26% w/w in soy oil. The size of the particles was determined by admixing 10 g of the preparation with 100 ml of hexane and passing this through 38, 30, and 20 micron-sized screens with agitation, while rinsing the particles through the screens with solvent. Any particles larger than the mesh size of the screen are retained on the screen with such a procedure. Less than 0.1% of the weight of the ascorbic acid particles was retained on any screen, showing that more than 99% was less than 20 microns in size.

A representative portion of the particles passing the 20-micron screen was mixed with castor oil, placed on a microscope slide, and examined using a lens piece which permits sizing of the particles. The particles in twelve random fields were counted according to size, and it was found that 84% were less than 5 microns, 13% between 5 and 10 microns, and 3% between 10 and 20 microns. The particles had irregular shapes. No commercial preparation of ascorbic acid is known which has such a concentration of less than 20-micron sized particles.

The same particle-size distribution may be obtained with lesser and greater percentages of ascorbic acid in the medium, e.g., in the oleogenous medium. As the concentration becomes greater, the suspension becomes thicker and more difficult to mix into the material to be stabilized. Concentrations up to about 35% are preferred, but higher concentrations are within the scope of this invention. Lower concentrations, such as 1% or 5%, are practical but less advantageous because the additional medium serves little useful purpose. It is the ascorbic acid particles per se or suspended in a medium in which they are insoluble which is the operative antioxidant and anti-fading component, and the concentration is incidental except in the ultimate vehicle which is to be stabilized.

It should be noted that the particles all had irregular surfaces and shapes, indicating fracture and exposure of surfaces to the medium in which it was milled. It is believed that this increases effectiveness of the particles, as well as their ability to be wet by the milling medium, thereby increasing their effectiveness as compared with a dry powder added directly to the oil to be stabilized.

The milling medium is not critical, although preferably oleogenous, provided that it does not dissolve the solid ascorbic acid particles, and need only be compatible with the oil or food to be stabilized, and edible when intended for use in a product to be ingested. Likewise, the concentration of ascorbic acid in the vehicle is not critical, although preferred levels are between about 10% or 20% and 35%, and practical levels range from 5% to 50%.

EXAMPLE 7

Stabilization of Chicken Fat with the Ascorbic Acid Suspension of Example 6, and Mixtures Thereof with Sage Extract Chicken fat was rendered from a whole carcass, separated from the broth, filtered, and dosed as shown in Table 7-1. The sage extract was Herbalox (R), Type S, made by Kalsec. It, like rosemary, is representative of the antioxidant power of Labiatae extracts.

The synergistic effect of the combination of sage and uAA should be noted, since the uAA increases the effectiveness of the sage by (6.64−1.81)/(2.59−1.00)=4.83/1.59=300%. Tocopherols at doses as low as 0.02% also are highly effective in combination with uAA, and in combination with uAA plus rosemary.

TABLE 7-1

Induction Times and Ratios to Control of Chicken Fat Stabilized with uAA, and with uAA plus Sage Extract.

| | dose | induct, hrs | ratio to control |
|---|---|---|---|
| control | 0 | 0.80 | 1.00 |
| uAA | 0.02 | 2.07 | 2.59 |
| sage | 0.02 | 1.45 | 1.81 |
| uAA + sage | 0.02 + 0.02 | 5.31 | 6.64 |

Turkey fat, another poultry fat, responds like chicken. Benefits obtained with pork and beef fats as substrates are similar. Where paprika, either ground or as an oleoresin, is combined with the fat-containing meat to make a sausage, the benefit of stabilization of the fat and carotenoid is combined. Rancidity is retarded by adding the uAA to fresh poultry meat, particularly in combination with Labiatae extracts.

EXAMPLE 8

Stabilization of Pigmented Fish Food

Discussion

The farming of trout and salmon has created a substantial market for manufactured feed which contains pigments which will color the flesh of the fish. Likewise, the need for highly-colored egg yolks has provided a market for both yellow and more orange pigments. Among those carotenoids now being used are canthaxanthin, astaxanthin, marigold xanthophylls, and paprika xanthophylls.

The animal diets contain fats, which should also be stabilized to provide optimal nutritional value (for example, salmon grow poorly when fed oxidized fats). This invention provides a means of stabilizing the fat and the pigment at the same time. Vitamin A, being related to the carotenoids, is also stabilized.

In this invention, pelleted trout food is made in the normal manner by extrusion, and it is then coated with a fat to which the premix of carotenoid, antioxidant, and optional emulsifier or bodying agent has been added. The carotenoid may be either in its free or esterified form. Although marine oils may be used successfully, they are less preferred than more saturated oils.

Example

A control mixture of 30% oleoresin paprika and 70% soy oil was made. A second test mixture containing 30% oleoresin paprika, 6% rosemary extract, 14% of the uAA of Example 6, and 50% soy oil, and a third test mixture consisting of 30% oleoresin paprika, 6% of rosemary extract, 14% of the uAA, and 50% lecithin were prepared. The stability of the oleoresins was evaluated on the Rancimat at 110° C./18 liters air/hr. Conductivity rather than induction time was used to measure stability, with the control having a conductivity of 222 and the test sample without lecithin a conductivity of 65 at the end of 17 hours. This shows the effectiveness of uAA. The lecithin sample foamed and conductivity could not be determined. The control sample had faded, the lecithin sample had become brownish, and the sample with only uAA and rosemary remained a bright red. The ⅔ lives of the color was also determined by placing 1 g samples in test tubes in an oven at 80° C. Since foaming could not occur, the ⅔ lives of all samples could be ascertained: control, 79 hours; uAA+rosemary, 132 hours; and uAA+rosemary+lecithin, 161 hours. The lecithin-containing sample had become brownish, the control orangish, and the uAA+rosemary retained a bright red color. This demonstrates that lecithin may be used in such a premix, but that it may cause discoloration.

This specific premix formula is not intended to be limiting, since more or less of the ingredients can be included. Only the uAA is essential to the stabilization of the color, but the rosemary or other Labiatae extract has a positive impact. Tea extract is another natural extract which may be used. Other antioxidants, such as ethoxyquin normally found in fish oils at 350 ppm, are compatible. Chelating agents, such as citric acid, may be useful if metal content is a problem.

EXAMPLE 9

Stabilization of a Marine Oil

Salmon oil was dosed with the 0.05% uAA of Example 6; with 0.05% uAA and 0.075% lecithin; and with 0.075% lecithin alone. At 95° C., the ratios of the induction times to the control, of the respective samples, were 1.98, 2.63, and 1.41. This shows that lecithin is compatible with uAA in a marine oil, where it also functions as an antioxidant. There is a slight synergistic effect.

EXAMPLE 10

Stabilization of Essential Oils and Cosmetics

Although the present invention is especially adapted to foods containing fats, it also has utility for the stabilization of essential oils. For example, orange oil was dosed with 0.05% of the uAA of Example 6, agitated one week in a loosely-closed container, and compared with the original oil which was undosed, but similarly exposed to oxidation. The control oil had developed a noticeable sharp, aldehyde-like aroma typical of oxidized orange oil. The dosed sample had not. Other oils high in hydrocarbons, such as black pepper, peppermint, dill, and lemon are particularly well stabilized by this invention.

If an essential oil is incorporated into a cosmetic, particularly into the fatty phase of a cosmetic like a cream or lipstick, both the essential oil and the fat are stabilized by the uAA. Even castor oil can benefit from the addition of this ascorbic acid composition.

EXAMPLE 11

Further Illustration of Stabilized Foods

Peanut butter is subject to oxidative degradation, having a shelf life of less than a year. Peanut butter was made in the conventional manner, without antioxidants, with 0.02% BHT, with 0.02% rosemary, and with 0.02% rosemary and 0.04% uAA of less than 38 microns in size. Peroxide values were determined on the fat after two months of storage at 85° F. The results were, respectively, 18.0, 10.4. 18.8, and <1. The uAA obviously had a tremendous effect, and the rosemary alone was without effect in this particular substrate.

The stability of safflower oil, which is highly unsaturated like peanut oil, also greatly benefits from the addition of uAA.

It is thus seen that the present invention provides a novel and advantageous form of solid particulate ascorbic acid and antioxidant compositions thereof, such products having increased antioxidant activity in fats, oils, carotenoids, and fatty foods, especially such materials and products as are exposed to oxidative stress, as well as a method of stabilizing such materials and products against oxidative discoloration, feeds and foodstuffs which may encounter oxidative stress stabilized with a composition of the invention, and a method of stabilizing a feed or foodstuff or flavoring with such a more effective form of ascorbic acid and/or ascorbic acid antioxidant composition of the invention. The stabilization of carotenoid pigments may thus advantageously be carried out. Synergistic effects are obtained by the incorporation of a natural antioxidant, e.g., such a fat- or oil-soluble antioxidant, in such compositions, methods, and products, and the antioxidant effectiveness of the antioxidant, antioxidant compositions, and methods of the invention is further enhanced by inclusion of a natural Labiatae antioxidant, tea extract, or a tocopherol therein, and antioxidant power and stabilization effectiveness may be even further improved by inclusion therein of a nonionic surface-active agent. All of the foregoing provide long-awaited solutions to previously-existing oxidation and instability problems not adequately solved by the prior art.

It is to be understood that the invention is not to be limited to the exact details of operation, or to the exact compositions, methods, procedures, or embodiments shown and described, as obvious modifications and equivalents will be apparent to one skilled in the art, and the invention is legally accorded to the appended claims.

I claim:

1. An antioxidant composition consisting essentially of solid particles of ascorbic acid which are less than about 38 microns in size on their largest dimension.

2. A composition of claim 1 wherein at least about 50% of the solid particles of ascorbic acid are less than about 10 microns in size on their largest dimension.

3. A composition of claim 1 wherein essentially all of the particles are about 20 microns or less on their largest dimension.

4. A composition of claim 1, comprising also a natural oil-soluble antioxidant.

5. The antioxidant composition of any one of claims 1 through 4, comprising also a non-ionic surface-active agent.

6. A composition of claim 5, wherein the surface-active agent is selected from the group consisting of glycerol mono-oleate, sorbitan trioleate, sorbitan mono-oleate, sorbitan monostearate, octaglycerol mono-oleate, and decaglycerol capric caprylate.

7. The antioxidant composition of any one of claims 1 through 4, comprising also a non-ionic surface-active agent, selected from the group consisting of
    a. mono and di glycerides of fatty acids,
    b. polyglycerides esters of fatty acids,
    c. mono and diglyceride esters further esterified with a dibasic organic acid taken from the class consisting of citric, lactic, and tartaric acids,
    d. acetylated mono and diglyceride esters further esterified with a dibasic organic acid taken from the class consisting of citric, lactic, and tartaric acids,
    e. sorbitan esters of fatty acids,
    f. propylene glycol esters of fatty acids, and
    h. lecithin.

8. An antioxidant composition consisting essentially of a suspension of solid ascorbic acid particles in a medium in which they are insoluble, the solid particles of ascorbic acid being less than about 38 microns in size on their largest dimension.

9. An antioxidant composition of claim 8, wherein at least about 50% of the solid particles of ascorbic acid are less than about 10 microns in size on their largest dimension.

10. An antioxidant composition of claim 8, wherein at least about 50% of the solid particles of ascorbic acid are less than about 5 microns in size on their largest dimension.

11. A composition of claim 8 wherein essentially all of the particles are about 20 microns or less on their largest dimension.

12. An antioxidant composition of claim 8, comprising also a natural oil-soluble antioxidant.

13. An antioxidant composition of claim 8, wherein the concentration of ascorbic acid particles of less than about 38 micron size in the medium is between about 5% and about 50% by weight.

14. An antioxidant composition of claim 8, wherein the ascorbic acid particles of less than 38 micron size have irregular shapes and their concentration in the medium is between about 20% and 35% by weight.

15. The antioxidant composition of any one of claims 8 through 14, wherein the composition comprises a nonionic surface-active agent.

16. A composition of claim 15, wherein the surface-active agent is selected from the group consisting of glycerol mono-oleate, sorbitan trioleate, sorbitan mono-oleate, sorbitan monostearate, octaglycerol mono-oleate, and decaglycerol capric caprylate.

17. The antioxidant composition of any claims 8 through 14, wherein the composition comprises a nonionic surface-active agent selected from the group consisting of
   a. mono and di glycerides of fatty acids,
   b. polyglyceride esters of fatty acids,
   c. mono and diglyceride esters further esterified with a dibasic organic acid taken from the class consisting of citric, lactic, and tartaric acids,
   d. acetylated mono and diglyceride esters further esterified with a dibasic organic acid taken from the class consisting of citric, lactic, and tartaric acids,
   e. sorbitan esters of fatty acids,
   f. propylene glycol esters of fatty acids, and
   g. lecithin.

18. The antioxidant composition of any one of claims 8 through 14 wherein the medium is an edible oleagenous medium.

19. The antioxidant composition of claim 18 wherein the composition comprises an orally-ingestible nonionic active agent selected from the group consisting of
   a. mono and di glycerides of fatty acids,
   b. polyglyceride esters of fatty acids,
   c. mono and diglyceride esters further esterified with a dibasic organic acid taken from the class consisting of citric, lactic, and tartaric acids,
   d. acetylated mono and diglyceride esters further esterified with a dibasic organic acid taken from the class consisting of citric, lactic, and tartaric acids,
   e. sorbitan esters of fatty acids,
   f. propylene glycol esters of fatty acids, and
   g. lecithin.

20. The method of protecting a substrate selected from the group consisting of an edible or other fat, oil, carotenoid, fatty food, or other substrate which is lipid in nature or which comprises a lipid phase, comprising the step of admixing the said substrate with an oxidtion-protective amount of a composition of any one of claims 1 through 4 or 8 through 15 wherein the medium is oleagenous.

21. The method of claim 20, wherein the amount of the composition employed is calculated to provide an amount of microcrystalline ascorbic acid in the substrate of at least about 0.002% by weight.

22. The method of claim 20, wherein a natural antioxidant taken from the class consisting of Labiatae extracts, tea extracts, and tocopherols is also added to the substrate or is present in the antioxidant composition employed.

23. The method of claim 20, wherein the composition comprises an orally-ingestible nonionic surface-active agent.

24. The method of claim 23, wherein the surface-active agent is selected from the group consisting of glycerol mono-oleate, sorbitan trioleate, sorbitan mono-oleate, sorbitan monostearate, octaglycerol mono-oleate, and decaglycerol capric caprylate.

25. The method of protecting a substrate selected from the group consisting of an edible fat, oil, and/or carotenoid by the addition thereto of at least about 0.002% by weight of solid ascorbic acid particles which are less than about 38 microns in size on their largest dimension.

26. The method of claim 25 wherein the protected substrate is a member selected from the group consisting of: soy oil; canola oil; peanut oil; sunflower oil; chicken fat; pork fat; turkey fat; beef fat; a marine oil; a paprika carotenoid; an annatto carotenoid; canthaxanthin; astaxanthin; and beta-carotene.

27. The method of any one of claims 22 through 26 wherein the composition comprises an orally-ingestible nonionic surface-active agent.

28. The method of claim 27, wherein the surface-active agent is selected from the group consisting of glycerol mono-oleate, sorbitan trioleate, sorbitan mono-oleate, sorbitan monostearate, octaglycerol mono-oleate, and decaglycerol capric caprylate.

29. The method of preparing an antioxidant composition consisting of the step of grinding solid ascorbic acid particles to a size less than about 38 microns on their largest dimension in a medium in which they are insoluble.

30. The method of preparing an antioxidant composition according to claim 29, wherein at least about 50% of the solid particles of ascorbic acid and ground to a size less than about ten minutes on their largest dimension.

31. The method of preparing an antioxidant composition according to claim 29, wherein at least about 50% of the solid particles of ascorbic acid are ground to a size less than about five microns on their largest dimension.

32. The method of preparing an antioxidant composition according to claim 29, wherein essentially all of the ascorbic acid particles are ground to a size of about twenty microns or less on their largest dimension.

33. The method of preparing an antioxidant composition according to claim 29, wherein the concentration of ascorbic acid particles, ground to a size less than about 38 microns on their largest dimension, in the medium is between about 5% and about 50% by weight.

34. The method of preparing an antioxidant composition according to claim 32, wherein the ascorbic acid particles are ground into irregular shapes and their concentration in the medium is between about 20% and about 35% by weight.

35. The method of preparing an antioxidant composition according to any one of claim 29 through 34, wherein a natural oil-soluble antioxidant is included in the ascorbic acid composition.

36. The method of any one of claims 29–34 in which the medium is oleagenous.

* * * * *

UNITED STATES PATENT AND TRADEMARK OFFICE
CERTIFICATE OF CORRECTION

PATENT NO. : 5,230,836

DATED : July 27, 1993

INVENTOR(S) : Paul H. Todd, Jr.

It is certified that error appears in the above-indentified patent and that said Letters Patent is hereby corrected as shown below:

Title page, item [56] "References Cited, U.S. PATENT DOCUMENTS, Col. 2,
    4th listing;, "5,077,869" should read -- 5,077,069 --.
Column 2, line 38; "so such" should read -- solvent, such --.
Column 7, line 11; "1/2 life:" should read -- 2/3 life: --.
Column 8, line 63; "have except" should read --have, except--.
Column 9, approximately line 26; "particles similar" should read
    -- particles, similar --.
Column 10, approximately line 14; "with fats" should read
    --with other fats --.
Column 10, approximately line 47; "Use Acid" should read
    -- Use of Dry Micron-size Ascorbic Acid --.
Column 12, TABLE 4-1, line 1; " $\frac{2}{3}$ " should read -- 2/3 --.
Column 12, TABLE 4-1, line 3; " $\frac{2}{3}$ " should read -- 2/3 --.
Column 12, line 57; "No. 5,059,435" should read -- 5,059,437 --.
Column 18, approximately line 27; "is legally" should read
    -- is therefore to be limited only by the full scope which
    can be legally --.
Column 18, line 63; "h. lecithin." should read --g. lecithin.--.

Column 19, line 30; "of any claims" should read -- of any one of
    claims --.

Column 19, line 47, "oleage-" should read -- oleagi- --.

Column 19, line 68; "oxidtion-" should read -- oxidation- --.

Column 20, line 2; "through 15" should read -- through 14 --.

Column 20, line 3; "oleagenous" should read -- oleaginous --.

UNITED STATES PATENT AND TRADEMARK OFFICE
CERTIFICATE OF CORRECTION

PATENT NO. : 5,230,836  
DATED : July 27, 1993  
INVENTOR(S) : Paul H. Todd, Jr.

Page 2 of 2

It is certified that error appears in the above-indentified patent and that said Letters Patent is hereby corrected as shown below:

```
Column 20, line 34; "claims 22 through 26: should read
     -- claims 21, 22, 25, and 26 --.
Column 22, line 4; "oleagenous" should read -- oleaginous --.
```

Signed and Sealed this

Twenty-sixth Day of July, 1994

Attest:

BRUCE LEHMAN

*Attesting Officer*         *Commissioner of Patents and Trademarks*